(12) United States Patent
Smart

(10) Patent No.: US 6,898,812 B2
(45) Date of Patent: May 31, 2005

(54) INFANT REFLUX MATTRESS SUSPENSE SYSTEM AND BED

(76) Inventor: Lucas M. Smart, 1701 E. Millcreek Cir., Salt Lake City, UT (US) 84106

(*) Notice: Subject to any disclaimer, the term of this patent is extended or adjusted under 35 U.S.C. 154(b) by 0 days.

(21) Appl. No.: 10/633,377

(22) Filed: Aug. 4, 2003

(65) Prior Publication Data

US 2005/0028286 A1 Feb. 10, 2005

(51) Int. Cl.⁷ .......................... A47D 7/03; A61G 7/002
(52) U.S. Cl. ................................ 5/655; 5/632; 5/603
(58) Field of Search ........................ 5/655, 603, 610, 5/630, 632–634, 424, 425, 427, 915; 128/845, 846, 875

(56) References Cited

U.S. PATENT DOCUMENTS

| | | | |
|---|---|---|---|
| 2,611,363 A | * | 9/1952 | Peters .......................... 5/603 |
| 2,647,561 A | * | 8/1953 | Szabo ........................ 297/313 |
| 2,697,480 A | | 12/1954 | Du Bois et al. |
| 2,777,138 A | * | 1/1957 | Gallagher ...................... 5/655 |
| 3,423,773 A | | 1/1969 | Yamate |
| 3,431,020 A | * | 3/1969 | Tyndall ....................... 297/467 |
| 3,759,252 A | * | 9/1973 | Berman ........................ 602/19 |
| 4,108,168 A | * | 8/1978 | Craig ........................... 602/24 |
| 4,441,221 A | | 4/1984 | Enste et al. |
| 4,471,767 A | | 9/1984 | Guimond |
| 4,566,449 A | | 1/1986 | Smith |
| 4,819,282 A | | 4/1989 | McArthur et al. |
| 4,977,630 A | | 12/1990 | Oswalt et al. |
| 5,127,422 A | | 7/1992 | Colon |
| 5,439,008 A | | 8/1995 | Bowman |
| 5,700,059 A | | 12/1997 | Moscot |
| 5,800,368 A | | 9/1998 | Klingemann et al. |
| 5,826,287 A | | 10/1998 | Tandrup |
| 6,023,802 A | | 2/2000 | King |
| 6,292,964 B1 | | 9/2001 | Rose et al. |

OTHER PUBLICATIONS

The Tucker Sling website Jun. 4, 2003.

* cited by examiner

*Primary Examiner*—Robert G. Santos
(74) *Attorney, Agent, or Firm*—Marcus G. Theodore

(57) ABSTRACT

An adjustable tilt bed with a post and strap securing system particularly applicable to the treatment of gastroesophageal reflux disease (GERD) in sleeping infants.

21 Claims, 5 Drawing Sheets

INFANT REFLUX MATTRESS SUSPENSE SYSTEM AND BED

BACKGROUND OF THE INVENTION

1. Field of Invention

The present invention relates to infant beds and suspension systems. In particular, it relates to a dual post strap suspense system for fixed angled or adjustable tilt beds particularly applicable to the treatment of gastroesophageal reflux disease (GERD) in infants. GERD is a common disease of infancy, which afflicts as many as 18% of otherwise healthy infants.[1] GERD is predominantly caused by relaxation of the lower oesophageal sphincter.[2] In other words, a doughnut shaped muscle located in the esophagus above the stomach, which constricts in healthy infants to keep stomach contents in place, fails or relaxes allowing stomach acids to travel back up the esophagus causing pain and tissue damage to the infant.

[1] A. E. Carroll. M. M. Garrison, and D. A. Christakis. A Systematic Review of Nonpharmacological and Nonsurgical Therapies for Gastroesophageal Reflux in Infants. Archives of Pediatrics & Adolescent Medicine. Feb. 1, 2002; 156(2): 109–113. [2] T I Omari, C P Barnett, M A Benninga, R Lontis, L Goodchild, R R Haslam, J Dent, and G P Davidson. Mechanisms of gastro-oesophageal reflux in preterm and term infants with reflux disease. GUT An Internation Journal of Gastroenterology and Hepatology, Oct. 1, 2002; 51(4): 575–479. [3] S. R. Orenstein. M. D. and P. F. Whittington, M. D. Positioning for prevention of infant gastro esophageal reflux Journal of PEDIATRICS 1983 October; 103(4): 534–7. [4] S. R. Orenstein. M. C. "Prone Positioning in infant gastroesophageal reflux: Is elevation of the head worth the trouble?" Journal of PEDIATRICS 1990; 117(Pt. 1); 185–187 [5] A. K. Ewer, M. E. James, and J. M. Tobin. Prone and left later positioning reduce gastro esophageal reflux in preterm infants. Archives of Disease in childhood Fetal Neonatal Edition 1999; 81:F201–F205 (November).

Clinical studies have concluded that infants suffering from GERD benefit from being positioned with their head elevated at approximately 30 degrees in a prone position.[3] Infants placed in an angled prone position cry less and sleep for longer periods of time.[4] Clinical studies have also concluded that symptoms of GERD are reduced when infants are placed to sleep on their left side.[5]

[1] A. E. Carroll. M. M. Garrison, and D. A. Christakis. A Systematic Review of Nonpharmacological and Nonsurgical Therapies for Gastroesophageal Reflux in Infants. Archives of Pediatrics & Adolescent Medicine. Feb. 1, 2002; 156(2): 109–113. [2] T I Omari, C P Barnett, M A Benninga, R Lontis, L Goodchild, R R Haslam, J Dent, and G P Davidson. Mechanisms of gastro-oesophageal reflux in preterm and term infants with reflux disease. GUT An Internation Journal of Gastroenterology and Hepatology, Oct. 1, 2002; 51(4): 575–479. [3] S. R. Orenstein. M. D. and P. F. Whittington, M. D. Positioning for prevention of infant gastro esophageal reflux Journal of PEDIATRICS 1983 October; 103(4): 534–7. [4] S. R. Orenstein. M. C. "Prone Positioning in infant gastroesophageal reflux: Is elevation of the head worth the trouble?" Journal of PEDIATRICS 1990; 117(Pt. 1); 185–187 [5] A. K. Ewer, M. E. James, and J. M. Tobin. Prone and left later positioning reduce gastro esophageal reflux in preterm infants. Archives of Disease in childhood Fetal Neonatal Edition 1999; 81:F201–F205 (November).

Notwithstanding these findings, the efficacy of recommending that infants be placed in an elevated position for sleeping has come under scrutiny by the medical community due in part to the cumbersome nature of the present devices designed to maintain infants in a prone position at a 30 degree angle, see footnote 4. None-the-less, inclined infant sleeping positions for infants with GERD are commonly recommended, see footnote 1. The present invention overcomes the cumbersome aspects of the prior inventions; thereby facilitating the inclined sleeping of infants with GERD.

2. Description of Related Art

Various tilted beds and suspension systems for infants are known. Some suspense systems specifically address infant GERD, such as the Tucker Sling™ produced by Tucker Designs Ltd, http://www.tuckerdesings.com, which fits around the upper part of an angled mattress like a contour sheet and has a diaper-shaped part attached that goes between a baby's legs and fastens around the waist with hook and loop strips such that the infant is secured to the angled mattress in a diaper like harness restricting its movements during sleep. The device makes it difficult to change the infant. It also provides no sidewalls or end walls to secure the infant in a safe environment, and is similar to devices considered too cumbersome by the medical community, see footnote 4.

Guimond, U.S. Pat. No. 4,471,767 discloses a therapeutic device to secure a child to an angled support surface via securing briefs and tethers. The infant is secured therein by two ropes. The ropes pose a significant risk of strangulation and cutting off the blood supply to limbs hands fingers etcetera, if the infant tips and becomes entangled as the child moves. The ropes could also prevent a child from reaching its arms down his/her side as infants naturally do during sleep, resulting in a less comfortable sleeping position.

If the diaper harness 25 is placed over a diaper, it will be very put and tend to tilt the child's lower torso up placing the spine in an unnatural position. It could cause a downward force on the child's abdomen and possibly neck and face. The wedge mattress is not adjustable and apparently is made out of a soft foam surface, which could add to the risk of smothering relative to the safety of a bassinet mattress. No catch mechanism is provided to protect the infant if the child slips out of the harness. Nor are there sidewalls for security or to protect child if the harness fails.

Colon, U.S. Pat. No. 5,127,422 discloses an anti-reflux saddle board with a differing strap system and mount. To use the saddle board, the child's legs are spread apart in an unnatural position, which could cause blood loss to the pubic area, deformity in the skeleton/muscle structure of the thighs waist and legs, and would be uncomfortable sleeping. When the straps are secured, the child's movement would be excessively restricted at the waist and near the shoulders. Few parents of a child with GERD could rest easy with their child tightly affixed to a mattress. Parents may fear that the child will not be able to move enough to cough up fluid or something obstructing its breathing path. The infant may also slump to the left or right in this device resulting in an unnatural, uncomfortable position that could be dangerous if the infant's air way became obstructed or the child spit up in his/her sleep. The straps may also prevent the child from reaching his/her arms down by its side as infants naturally might do during sleep, again resulting in a less comfortable sleeping position. The thin loose straps (only connected by hook and loop strips) could also become entangled and if the child fell from the center crotch support mechanism the child could strangle on the straps or fall onto an unsafe surface.

This device only reclines at two angels 30 and 45 degrees. Some infants with minor symptoms, or as they start overcoming GERD, may need less severe angles of repose. The device thus presents an infant with a "cold turkey" scenario, where the child goes from upright sleeping to flat sleeping, which may cause adjustment problems.

Another drawback is that the child sleeps on a hard flat washable plastic mattress, which may not be comfortable, preventing the child from sleeping. The hard plastic mattress may not breath possibly causing the child to suffer bedsores and possible infections.

Doran et al, U.S. Pat. No. 5,014,376 discloses a wedge shaped support mattress with a support blanket to secure the infant thereto. There is nothing to keep a child from sliding off the foam wedge. This foam type wedge may provide too soft a surface for safe infant sleep, as a child can smother itself by placing its face, face down on foam.

Bowman, U.S. Pat. No. 5,439,008 discloses an infant reflux restraint apparatus employing side straps, and a head positioning support attached to a wedge shaped mattress. The inner-tube like ring/pillow is designed for positioning an infant to sleep on its back, which is not the recommended GERD treatment position, see footnotes 3 and 5. The child's movements are also severely restricted by the securing straps. The lateral support pillows, 51, 52 located on either side of the sleeping infant, excessively restrain the child, could cause chafing and may prevent the infant from assuming a left side sleep position or lowering its arms. If the straps push up into the infant's armpits thus forcing the child's arms above its head, they could—over time—cause skeletal muscle problems.

Smith, U.S. Pat. No. 4,566,449 discloses an elevated infant positioner using cut-out templates to surround and secure an infant at an inclined angle. This device claims to overcome the excessive restraint shortcomings of other art but goes too far. The child is not actively held by anything but sidewalls and gravity so that a child could slump down and fall out of this device. This device is also made of foam, which may pose a smothering hazard. It also does not allow for widely adjustable mattress reclining angles. The child's movement side to side and its ability to put its arms up or down is restricted and the device may not encourage left side sleeping. This device would have a tendency to encase the child in insulation causing a significant increase in their risk of overheating, which may be a risk factor for Sudden Infant Death Syndrome (SIDS).

Klingemann et al, U.S. Pat. No. 5,800,368 discloses another elevated infant positioner using cut-out templates to surround and secure an infant at the inclined angle, and also includes a strap securing system. This device is similar to Smith, U.S. Pat. No. 4,566,449 and is subject to all of its shortcomings. It has the added risk of infant strangulation if an infant fell with its neck over the strap system.

Cited for general interest are: Enste et al, U.S. Pat. No. 4,441,221, which discloses a child support wedge and strap system for children having multiple injuries and/or severe handicaps.

Rose et al, U.S. Pat. No. 6,292,964 discloses a wedge pillow and cushions employing no restraining or suspension equipment making it virtually useless for infants. It is primarily employed for use by adults to provide lower back and neck support.

King, U.S. Pat. No. 6,023,802 discloses an infant sleeper with sidewalls to secure an infant to a horizontal mattress support surface. The mattress reclining angle is possibly insufficient to assist in GERD therapy and is not adjustable. The straps would not hold a child therein, and the device has no safety catch mechanism. The mattress is made of foam and therefore exposes the infant to the risk of smothering and overheating.

Moscot, U.S. Pat. No. 5,700,059 discloses a vertical baby support for simulating the ordinary front and back holding positions of a baby. It does not appear to address GERD and the angle at which it holds a child appears to be too steep for prolonged sleeping and may exacerbate GERD, see footnote 4. Its suspension mechanism is restrictive and may pose the threat of strangulation.

Oswalt et al., U.S. Pat. No. 4,977,630 discloses an angled patient mover with restraints. It is geared toward use with young children rather than infants and apparently addresses mobilizing sick and injured children for transport purpose to, from, and within hospitals.

McArthur et al, U.S. Pat. No. 4,819,282 discloses a tilting mechanism for use with an infant bassinet. This device only tilts a bassinet mattress and does not secure an infant on that mattress. This device has complicated exposed metal parts that a child could be injured on if the child falls off the mattress and crawls under the inclined plane.

Yamate, U.S. Pat. No. 3,423,773 discloses an orthopedic device with a hinged bed and saddle with straps to secure thereto a patient with immobilized legs. It is probably too restrictive at waist and upper torso for GERD treatment, see footnote 4, and requires an unnatural spread leg position. To hold a child and prevent movement side to side, the waist belt would have to be secured very tightly, or the child could still slump by bending at the waist. A soft surface pillow could also be dangerous for stomach sleeping. It has no sidewalls or catch mechanism for safety if the strap suspension system fails. It also employs thin belts, which could pose a significant risk of strangulation.

Tandrup, U.S. Pat. No. 5,826,287 discloses an infant support and positioning system incorporating three releasably attachable cushions associated with a strapping system. It does not claim to address GERD, but addresses muscle tone issues and the need to secure children in car seats that are too large for them. No angled mattress support is incorporated. It also uses foam filled cylinders, which may pose an infant smothering hazard.

E. M. Du Bois et al, U.S. Pat. No. 2,697,480 discloses an angled shampoo chair to keep soapy water out of the eyes of children.

The present invention described below provides an improved infant reflux adjustable strap suspense and GERD treatment infant mattress system.

OBJECTIVES OF THE INVENTION

The objectives of the present invention are to provide:

1. a secure non-overly restrictive GERD treatment device allowing sleep movement such that the blood supply is not cut off to arms, legs or hands, other devices could apparently cause strangulation.
2. a safe infant sleeping environment to allay parent's fears.
3. a suspense system for an adjustable angled mattress, wherein the angle of repose may be changed as required for GERD treatment.
4. a comfortable GERD treatment device, which encourages an infant's sleep; and thereby allows parents to relax.

New parents have many fears concerning the health of their infant. These are exacerbated when the infant suffers from GERD. Because of these fears the parent is very anxious and sensitive to the infant's sleeping position and the child's immediate sleeping environment. The literature on infant sleep is very specific, even for healthy infants. Parents are instructed to place their children in a bassinet or crib with a firm mattress and thin taut sheet, all surfaces the infant may come in contact with are supposed to be firm to eliminate the possibility that the child may press his or her face against soft material and thereby obstruct their breathing passages. Parents are told to use one thin blanket plus pajamas, with no stuffed animals or fluffy covers. The room temperature is to be kept below 75 degrees Fahrenheit.

The device described below is designed to provide flexibility to meet a GERD infant's sleep requirements and calm its parents' fears.

SUMMARY OF THE INVENTION

The present invention comprises in its simplest embodiment a strap and dual post suspension system secured to the mattress on either side of an infant lying on either a fixed angled or variably inclined mattress or inclined crib mattress. A suspension strap is attached to the side posts and passes between an infant's legs to support it from the crotch. These side posts extend from the mattress surface sufficiently on either side of the chest of the suspended infant to prevent it from turning laterally and falling down the inclined mattress. They are also preferably structured to secure the suspension strap above the mattress surface to allow the infant to position its arms either above or below the strap as discussed below. Preferably the side post positioning and suspension straps are adjustable to accommodate different sized infants.

The side posts are attached with a mattress securing structure, such as an adjustable H shaped harness with hooked ends structured to secure to the top of the mattress. The securing structure positions the posts spaced apart on either side of a reclining infant. The pair of laterally adjustable side posts are adjustably attached to the securing structure with extenders, and preferably are of a height slightly higher than the reclining infant.

To use the simplified strap and post suspension system, the infant mattress has one end angled upward, preferably from between zero and 30 degrees. The securing harness is then positioned over the elevated end of the mattress to position the side posts along each side of a reclining infant. The suspense strap is then attached to the side posts and the infant is positioned thereon such that the strap passes between the infant's legs to support it from the crotch between the side posts. This three point holding system allows an infant sufficient movement to facilitate sleep, while securing the infant to the angled mattress.

The strap and post suspension system invention can also be incorporated as part of a fixed angle or tiltable adjustable bed to treat GERD. These GERD beds generally comprise either a fixed angled wedge shaped mattress, or alternatively, a mattress whose angle may varied. The adjustable angled mattress embodiment employs a base hingedly attached to a mattress support secured at a desired angle with securing structure, such as an adjustable locking hinge. The mattress support is capable of being held at a desired angle between zero and 30 degrees. It supports a mattress placed and secured thereon. When traveling, the mattress support and base are closed at the zero angle position to minimize its thickness to aid in transport.

In a preferred adjustable tilting embodiment, the base is hingedly attached to the mattress support and adjustably secured at the desired angle with tilting means. The presently recommended 30 degree angle for GERD treatment may be too steep, so the device can be readily adjusted to accommodate less acute angles. This is particularly important when the child ages and starts to outgrow its GERD condition. The device can gradually be reduced to adjust to sleeping on a conventional flat mattress.

In one tilting variation, a pair of pivoting supports with one end pivotally attached to the base and the other end having a hole, which is aligned and secured in one of a series of positioning holes in the mattress support secure the mattress support via a pin system to hold it at the desired angle between zero and 30 degrees.

In another preferred tilting embodiment, an adjustable extendable telescoping arm support system is included. It has one end attached to the base and the other end adjustably extendably secured to the mattress support to secure the mattress support at varying desired angles.

A washable mattress firm, enough to prevent interference with an infant's breathing when sleeping on its stomach, is removably mounted onto the mattress support. The mattress has slots spaced apart on both sides of the segment where an infant would lay.

A pair of laterally adjustable side posts preferably of a length slightly higher than the height of a reclining infant is attached to either the fixed angled mattress or to the mattress support and secured thereto a distance spaced sufficiently apart to prevent an infant, positioned there between on the support strap, from falling horizontally down the inclined mattress.

For the adjustable tilt mattress system, a reclining mattress with holes therein is removably mounted onto the mattress support such that the holes are aligned to accommodate the adjustable side posts attached to the mattress support. This allows the mattress to be removed for cleaning. The mattress is firm with no soft surfaces, which pose a smothering risk. It is also designed to be covered by a taut sheet. Preferably the mattress is constructed of a cleanable material and sized to be covered by a conventional removable sheet also having holes therein sized to accommodate the adjustable positioned side posts. The sheet may then be removed for washing periodically and the mattress cleaned.

A suspense strap is attached to the side posts of a length and width such that it is capable of passing between an infant's legs to support the infant on the reclining mattress. By placing the child's left leg under the strap and right leg over the strap the child is encouraged (although not forced) to sleep on its left side (possibly the preferred GERD position), see footnotes 4 and 5. However, to prevent bedsores, the infant may be encouraged to sleep on either side by reversing the leg positions. In addition, the straps allow the infant to be placed on its back for sleeping. The device thus provides flexibility for securing the infant on the angled mattress and encourages the child to sleep on its left side, by placing its right leg over the harness strap.

The center posts come straight up from the mattress and secure the harness straps. They hold the straps on the posts with stops, which preferably hold the bottom of the strap approximately 2 inches above the surface of the angled mattress. Thus the infant can position its arms reaching above or below its waist without risking strap entanglement or blood circulation loss. Also, the child can safely hold its arms above the head or below the waist in whatever position it feels is most comfortable and natural.

The sliding center post design makes the invention fully adjustable to accommodate different sized infants via the interchange of different sized adjustable straps. For example, the straps on the posts can be exchanged for thinner straps (1 inch), the posts slid in and, and the foot support moved up to accommodate a very small severely premature infant. Thicker straps (2 inches) may be substituted with the opposite adjustments to accommodate a larger child. Thus, the device can be adjusted as the child grows.

In one preferred tilting bed embodiment, an adjustable safety board is attached to the mattress support and positioned below the suspended infant's feet to prevent the upper body and head of the infant from sliding down and being caught by the suspense strap in the event the infant disengages his/her legs from the suspense strap. Preferably, the adjustable suspense strap is removably mounted to the pegs for cleaning. The straps are sized thick enough to not put life threatening pressure on an infant's neck in the event of accidental contact; thereby preventing strangulation in the event of failure. This is unlikely because the straps are firmly attached to the posts and made of strong nylon or plastic, and the adjustable foot support would catch the child in the event of accidental failure.

The base is of sufficient weight and width to prevent tilting of the adjustable bed when supporting an infant, and is preferably hingedly attached to the mattress support. The reclining infant can therefore be supported at any angle from 30 degrees or less. The angle selected is dependent upon the severity of the GERD condition and a doctor's recommendation. As the infant matures and the GERD subsides, the angle of the bed is gradually lowered over time. The pivoting support is structured to secure the mattress support to the base at a zero degree angle in a closed position for transport. To aid in transport, a handle or hand cut-out is attached to the mattress support for carrying the adjustable bed in the closed position.

In another preferred embodiment, parallel sideboards are attached to the adjustable angled mattress support on either side of the posts to prevent a suspended infant from being accidentally hit from the side, and provide a draft screen. These side walls are safe and provide peace of mind to the parent that the infant is secure when placed in the invention.

A handle may be attached to the mattress support for carrying the adjustable angled bed embodiment in the closed position.

Thus constructed, the device provides adjustability of the angle of repose; adjustability of the center posts to accommodate various sized infants; adjustability of the suspense strap length, and adjustability of foot safety support to extend the same as the child grows. All removable parts are preferably constructed with a minimum 1.75" diameter size so that no stray parts pose a choking hazard to the child.

The present invention is therefore particularly adapted to provide a fixed or adjustable angled reclining bed and support system for infants suffering from GERD.

BRIEF DESRIPTION OF THE DRAWINGS

DESCRIPTION OF THE ILLUSTRATED EMBODIMENTS

Figure 1:
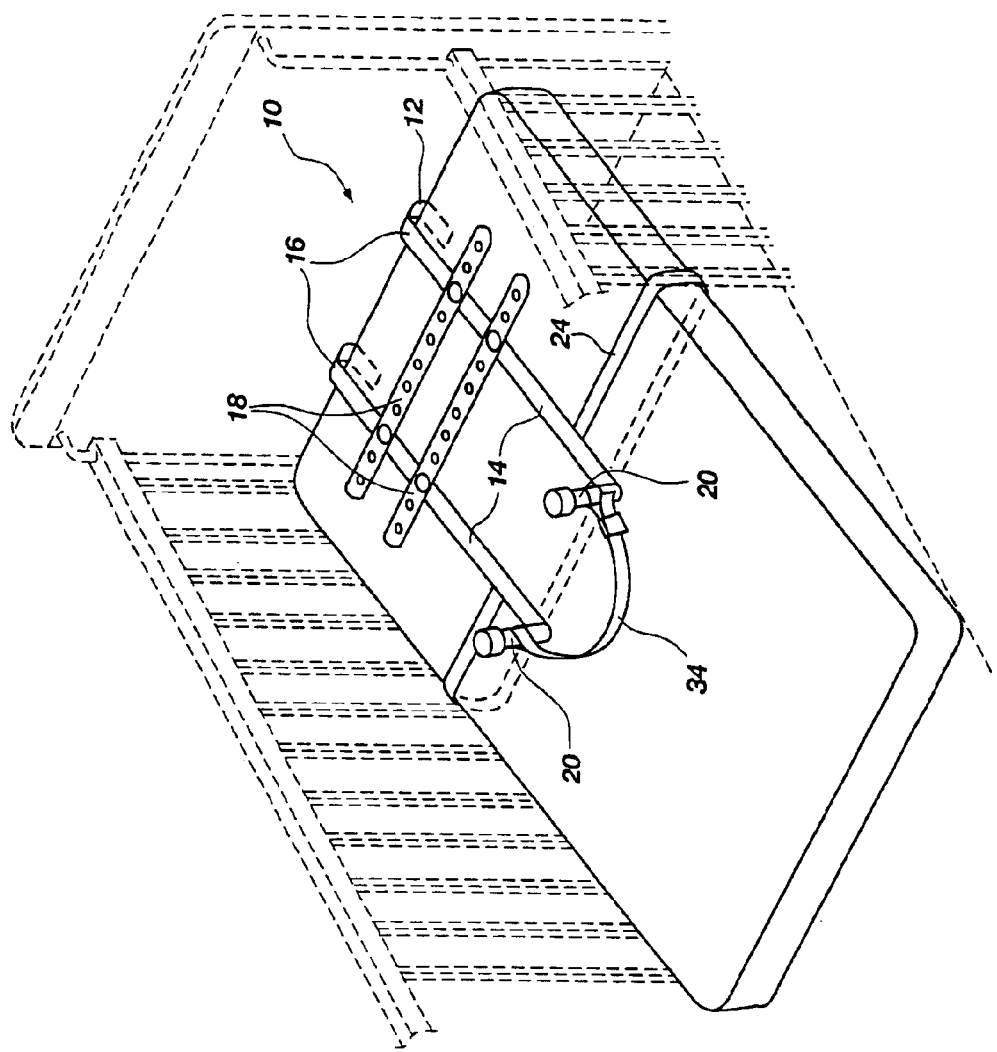
FIG. 1 is a perspective view of a preferred embodiment of the invention.

As shown in FIG. 1, in its simplest embodiment, the infant reflux mattress suspense system 10 comprises mattress securing structure means 12 affixed to an elevated end of an infant mattress. The infant mattress is inclined at a desired angle 30 degrees or less, depending on the infant's condition. Usually this is done via supports placed under the end of the mattress.

The mattress securing structure means 12 extends along each side of a reclining infant placed on an inclined mattress. One preferred embodiment of the mattress securing structure means 12 is the H shaped harness shown in FIG. 1. It has variable width side bars 14 extending from the top of the elevated mattress to the torso of the infant. These side bars 14 have hooked ends 16 structured to pass over the elevated end of the mattress to secure the H shaped harness to the elevated mattress.

A pair of interconnecting notched parallel lateral supports 18 is adjustably attached to the side bars 14 via screws and holes to position the supports 18 out of the way above the infant's head while adjustably providing the desired width of the side bars 16 along the sides of the infant.

Side posts 20 are attached to the mattress securing structure 12 side bars 14 on both sides of the infant proximate its chest, when suspended.

An adjustable suspension strap 34 is attached to the side posts 20. It is of sufficient length and width to pass between an infant's legs to support it from the crotch. The side posts 20 extend from the mattress surface sufficiently on either side of the chest of the suspended infant to prevent it from turning laterally and disengaging from the strap and falling down the inclined mattress.

The infant reflux mattress suspense system may include a mattress securing strap 24 affixed to the side bars 14 of a length sufficient to pass around the mattress to secure the harness 12 thereto. This embodiment is particularly suited for travel usage and adaptation of any inclined infant mattress.

Figure 2:
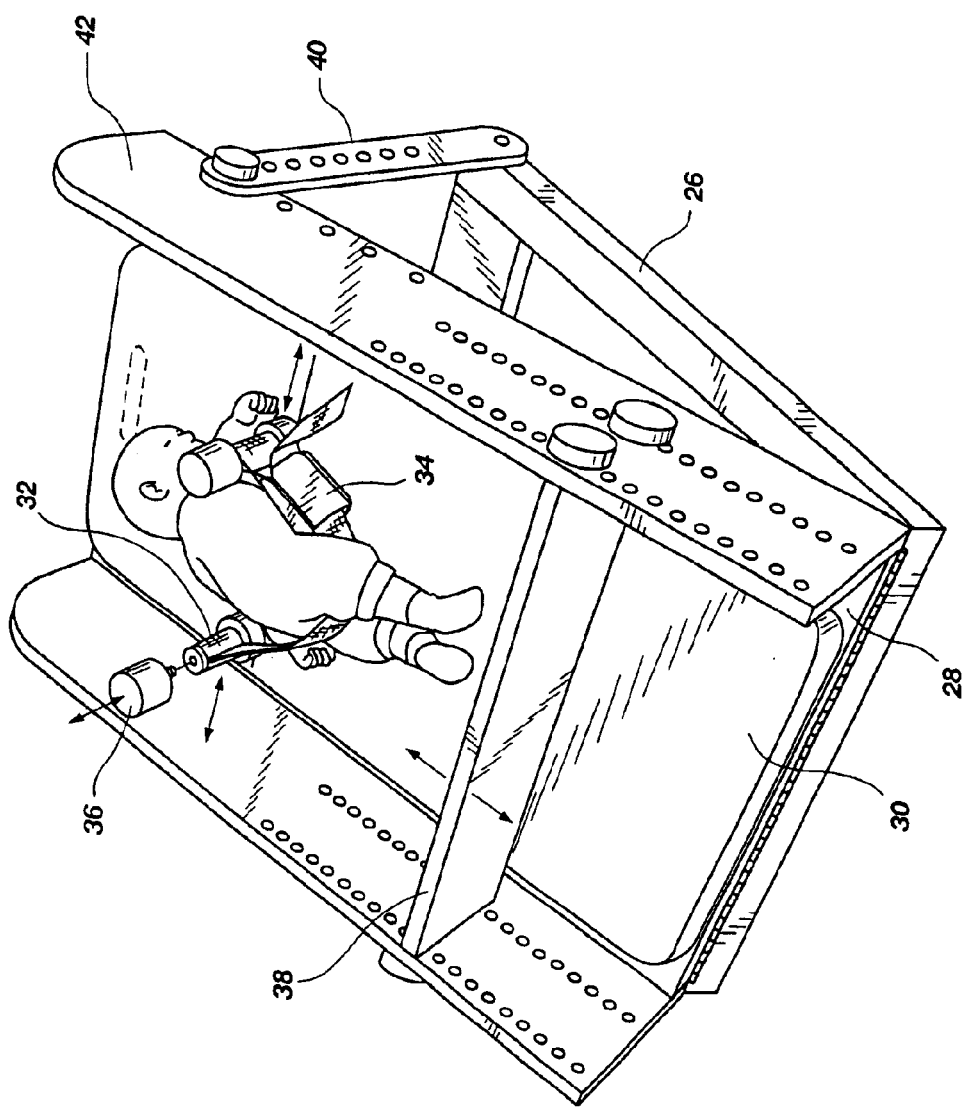
FIG. 2 is a perspective view of another preferred embodiment of the invention.
Figure 3:
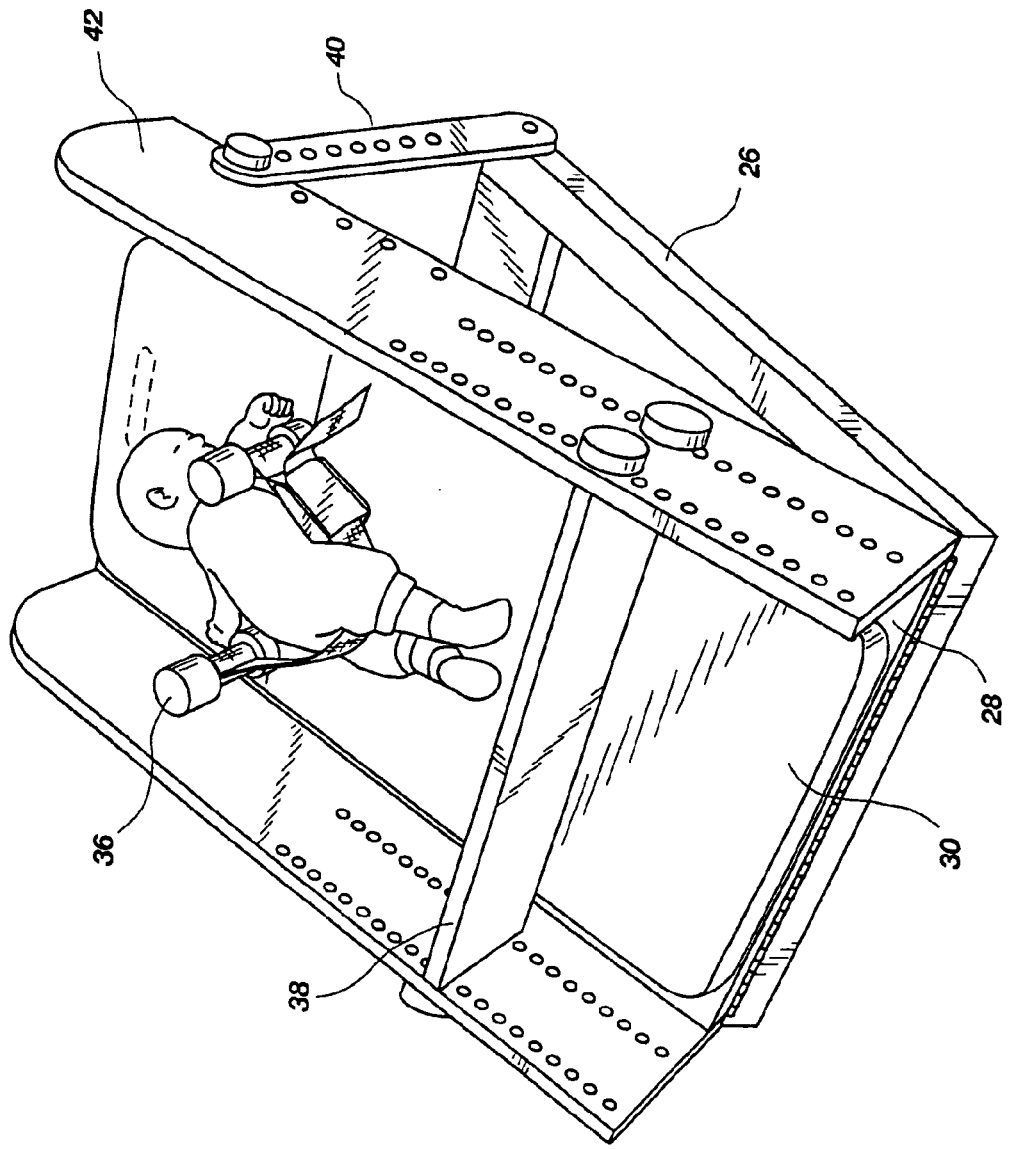
FIG. 3 is a perspective view of the embodiment of the invention shown in FIG. 2 supporting an infant.

A preferred embodiment of an adjustable infant reflux mattress bed and suspense system is shown in FIG. 2. The invention 10 comprises a base 26 with a hinged adjustable angled bed frame 28 onto which a firm mattress 30 is affixed to prevent smothering of an infant lying on its stomach. Two adjustable posts 32 are affixed to the bed frame 28 extending and passing through the mattress 30 to position the side posts 32 above the mattress surface and spaced sufficiently apart for an infant to lie and be secured there between. An adjustable suspension strap 34 is attached to the posts 32 and adapted to fit over the infant's left leg, pass between both legs, and pass under the infant's right leg to encourage sleep on his left side between the posts 32 as shown in FIG. 3. This suspension strap 34 is interchangeable and selected of a width to provide proper support of the infant without unduly interfering with its movements. Usually, the posts 32 include a cap 36 to secure the suspension strap 34 to the posts 32 and a riser 33 numbered in FIG. 4 to elevate the strap 34 above the surface of the mattress 30, such that an infant can place its hands above or below the strap 34.

A safety board 38 to catch the infant in the event he/she wiggles out of the suspension strap 34 is placed beneath the infant. A pair of adjustable slideable risers 40 is associated with the base 26 and bed frame 28 to secure the mattress 30 at the desired angle. The bed frame 28 is adjusted originally to an angle of approximately 30 degrees via the adjustable frame risers 40. It is thereafter progressively lowered as the infant outgrows gastroesophageal reflux as directed by a doctor.

Side boards 42 are affixed to the frame 28 to prevent drafts and accidental contact with the reclining infant.

FIG. 3 is a perspective view of the embodiment shown in FIG. 2 with the adjustable suspension strap 34 secured to the posts 32 with the caps 36.

Figure 4:
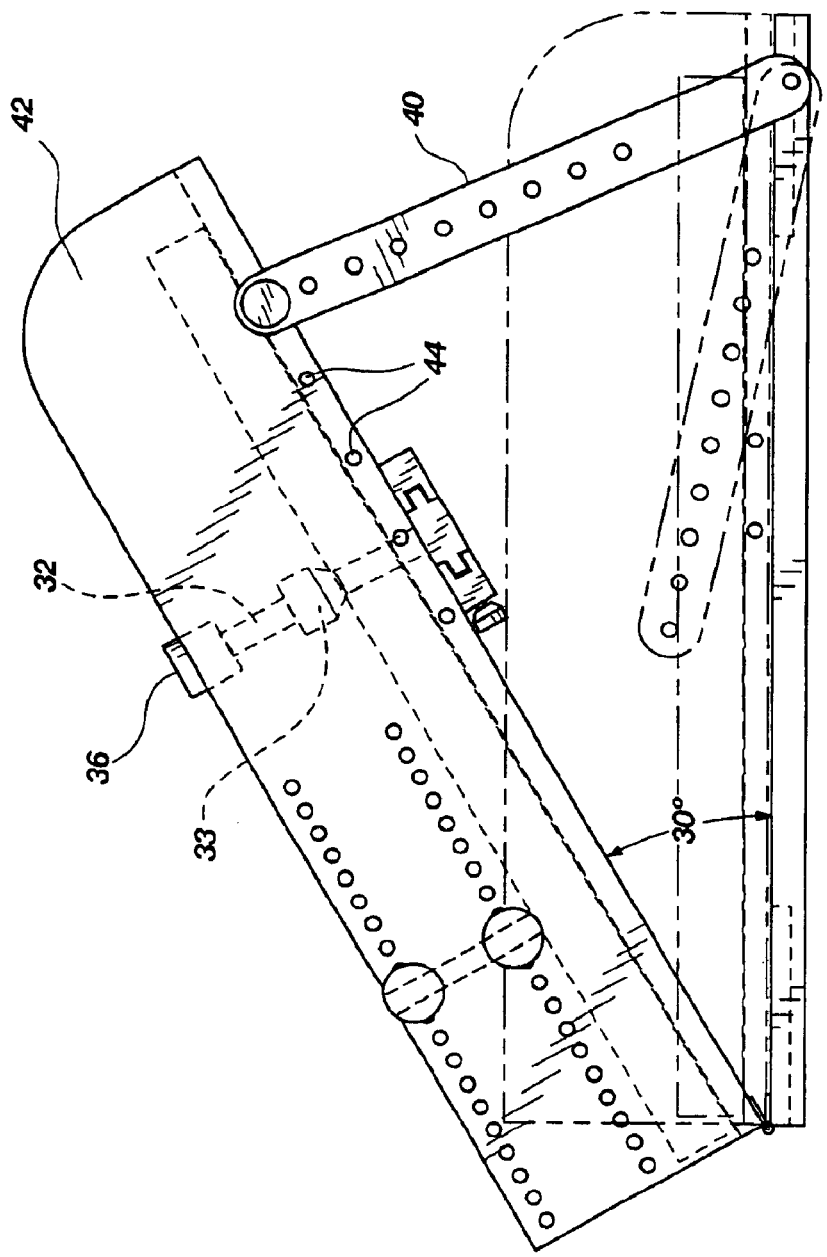
FIG. 4 is a side view of the embodiment of the invention shown in FIG. 3.

FIG. 4 is a side view of the invention of FIGS. 2 and 3 showing the above parts in an elevated or a closed position for traveling. The arm 40 is pivotally attached to the frame 28 via a series of adjustment holes 44 to secure the frame 28 at the desired angle.

Figure 5:
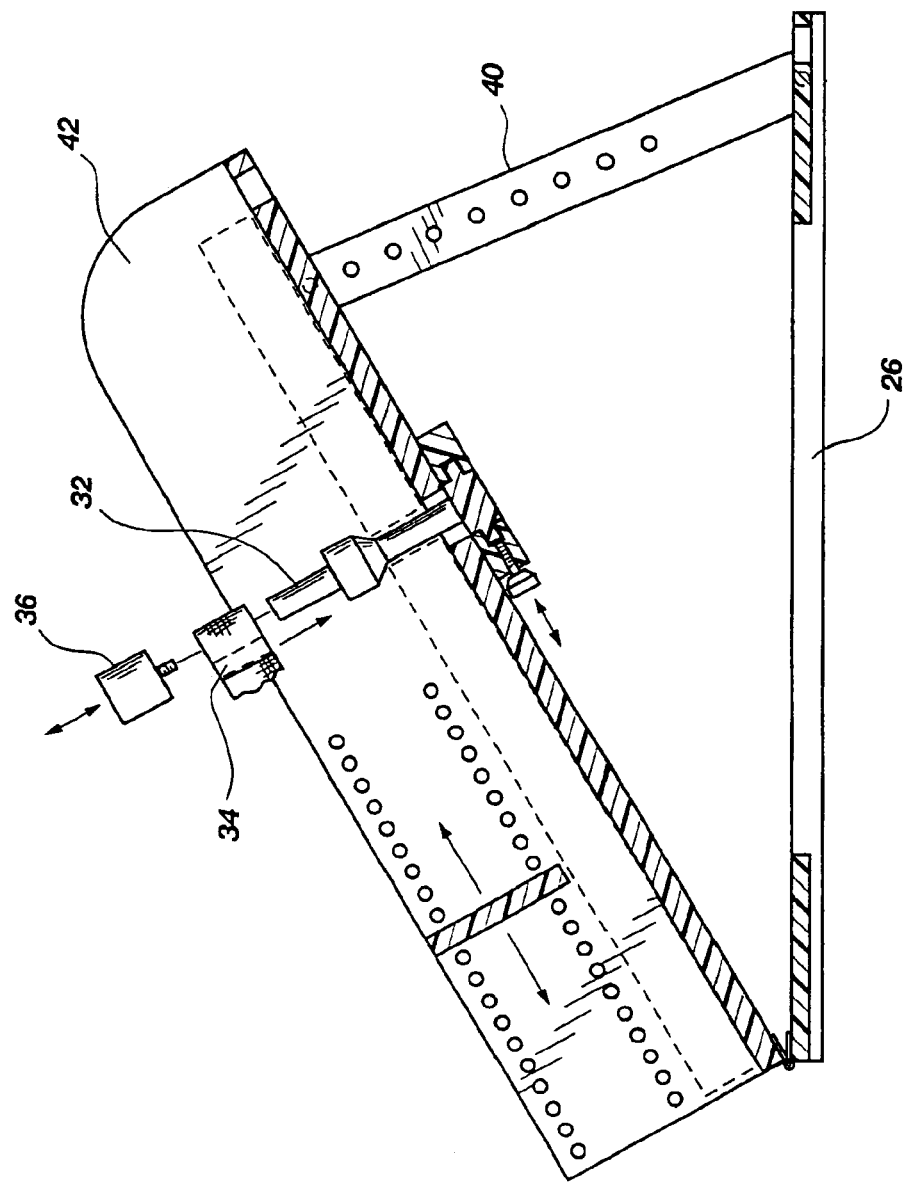
FIG. 5 is a cut away view of the embodiment of the invention shown in FIG. 4.

FIG. 5 is a cut away side view of the invention of FIGS. 2 and 3 disclosing how the caps 36 separate from the post 32 to allow removal and interchange of different straps 34.

The components are constructed of washable materials that can be disassembled and washed periodically. They must be strong enough to support the weight of the infant, and are preferably constructed of lightweight materials, such as reinforced nylon, plastic, aluminum, wood, steel, etc. which are light to transport. The assembled components are preferably also conventionally sized and designed for use in standard sized bassinets, and cribs.

The above description and specification should not be construed as limiting the scope of the invention but as merely providing illustrations of some of the presently preferred embodiments of this invention. Thus, the scope of the invention should be determined by the appended claims and their legal equivalents rather than by the examples given.

I claim:

1. An infant reflux mattress suspense system comprising:
   a. mattress securing structure means affixed to an elevated end of an infant mattress and extending around and along each laterally adjustable side of a reclining infant,
   b. side posts attached to the mattress securing structure on both sides of the infant proximate its chest and extending from the mattress surface sufficiently on either side of the chest of the suspended infant to prevent it from turning laterally, and
   c. a suspension strap attached to the side posts of sufficient length and width extedning downwardly between the posts toward the end of the mattress opposite said elevated end to pass between an infant's legs to support it from the crotch between the side posts, such that the side posts and suspension strap allow infant movement during sleep, but prevent the infant from disengaging and falling down the inclined mattress.

2. An infant reflux mattress suspense system according to claim 1, wherein the mattress securing means comprises:
   a. an H shaped harness with variable width,
   b. side bars extending from proximately the top of the elevated mattress to the sides of the infant,
   c. hooked ends attached to the top of the side bars structured to pass over the elevated end of the mattress and secure the H shaped harness to the elevated mattress, and
   d. A pair of interconnecting parallel lateral supports attached to the side bars in a position above the infant's head to adjustably secure the width of the side bars at the desired position along either side of the chest of a suspended infant.

3. An infant reflux mattress suspense system according to claim 2, including a securing strap affixed to the side bars of a length sufficient to pass around the mattress to secure the harness thereto, and the suspension strap is adjustable.

4. An infant reflux suspense system and bed for infants suffering from gastro esophageal reflux disease comprising:
   a. an angled mattress sized to accommodate a sleeping infant with an angle incline of between zero and 30 degrees and firm enough to prevent interference with an infant's breathing when sleeping on its stomach including slots aligned to accommodate,
   b. a pair of laterally adjustable or fixed side posts of a length approximately the height of a reclining infant including structure to attached to the mattress and spaced sufficiently apart to prevent an infant positioned there between from falling down the mattress sideways, and
   c. a suspense strap attached to the side posts such of sufficient length and width extending downwardly between the posts toward the end of the matress opposite said elevated end that it passes between an infant's legs to support the infant on the angled mattress such that the side posts and suspension strap allow infant movement during sleep, but prevent the infant from disengaging and falling down the inclined mattress.

5. An infant reflux suspense system and bed according to claim 4, wherein the angled mattress comprises:
   a. a base with attachment structure to tiltably secure to,
   b. a pivoting mattress support capable of being held at a varying angles between zero and 30 degrees, and
   c. a reclining mattress with holes therein mounted on the mattress support such that the holes are aligned to accommodate the slideably aligned side posts.

6. An infant reflux suspense system and bed according to claim 5, including an adjustable safety board attached to the mattress support positioned below the suspended infant's feet to prevent the infant from sliding down and being caught by the suspense strap in the event the infant disengages his/her legs from the suspense strap.

7. An infant reflux suspense system and bed according to claim 5, wherein the suspense strap is removably mounted to the posts for cleaning and interchangeable with different sized straps to accommodate varying sized infants.

8. An it reflux suspense system and bed according to claim 7, wherein the suspense strap is mounted to the posts sufficiently above the mattress to allow an infant to position its arms reaching above or below its waist without risking strap entanglement or blood circulation loss.

9. An infant reflux suspense system and bed according to claim 5, wherein the mattress is removably mounted to the mattress support.

10. An infant reflux suspense system and bed according to claim 5, wherein the base is of sufficient weight and width to prevent tilting of the adjustable bed when supporting an infant.

11. An infant reflux suspense system and bed according to claim 5, wherein base is hingedly attached to the mattress support, and includes a pivoting support with one end attached to the base and the other end associated with the mattress support to secure the mattress support at the desired angle.

12. An infant reflux suspense system and bed according to claim 5, wherein the pivoting support is structured to secure the mattress support to the base at a zero degree angle in a closed position for transport.

13. An infant reflux suspense system and bed according to claim 5, including a handle attached to the mattress support for carrying the adjustable bed in the closed position.

14. An infant reflux suspense system and bed according to claim 8, wherein the mattress is constructed of a cleanable material and sized to be covered by a removable sheet having holes sized to accommodate the posts.

15. An infant reflux suspense system and bed according to claim 5, including parallel sideboards attached to the mattress support on either side of the posts to prevent a suspended infant from being accidentally hit from the side, and provide a draft screen.

16. An infant reflux suspense system and tiltable bed for infants suffering from gastro esophageal reflux disease comprising:
   a. a base hingedly attached to,
   b. a mattress support with
   c. securing means capable of holding the mattress support a desired angle between zero and 30 degrees,
   d. a washable reclining mattress firm enough to prevent interference with an infant's breathing when sleeping on its stomach with slots spaced apart on both sides of the segment where an infant would lie removably mounted on the mattress support, e. a pair of laterally adjustable side posts of a length slightly higher than a reclining infant attached to the mattress support spaced sufficiently apart pass through the reclining mattress slots to secure at a desired position along the sides of an infant to prevent an infant positioned there between from falling down the mattress sideways, f. parallel sideboards attached to the mattress support on either side of the mattress outside the posts to prevent a suspended infant from being accidentally hit from the side, and provide a draft screen, g. an adjustable safety board attached to the mattress parallel sideboards positioned below the suspended infant's feet to prevent the infant from sliding down and being caught by the suspense strap in the event the infant disengages his/her legs from the suspense strap, and h. a suspense strap removably mounted to the side posts sufficiently above the mattress such that it passes between an infant's legs to support the infant on the reclining mattress and allows an infant to position its arms reaching above or below its waist without risking strap entanglement or blood circulation loss.

17. An infant reflux suspense system and tiltable bed according to claim 16, wherein the base is of sufficient weight and width to prevent tilting of the adjustable bed when supporting an infant.

18. An infant reflux suspense system and tiltable bed according to claim 16, including a pivoting support with one end attached to the base and the other end associated with the mattress support to secure the mattress support at the desired angle.

19. An infant reflux suspense system and tiltable bed according to claim 16, wherein the pivoting support is structured to secure the mattress support to the base at a zero degree angle in a closed position for transport.

20. An infant reflux suspense system and tiltable bed according to claim 19, including a handle attached to the mattress support for carrying the adjustable bed in the closed position.

21. An infant reflux suspense system and tiltable bed according to claim 16, wherein the mattress is sized to be covered by a conventional sized removable sheet having holes therein sized to accommodate the movable posts.

* * * * *